United States Patent [19]

Kos

[11] Patent Number: 5,686,625
[45] Date of Patent: Nov. 11, 1997

[54] PROCESS FOR THE PREPARATION OF N-SUBSTITUTED GLYCINE ACIDS OR GLYCINE ESTERS AND THE USE OF THE PROCESS FOR INDIGO SYNTHESIS

[75] Inventor: Carlo Kos, Leonding, Austria

[73] Assignee: DSM Chemie Linz GmbH, Linz, Austria

[21] Appl. No.: 652,445

[22] PCT Filed: Dec. 21, 1994

[86] PCT No.: PCT/EP94/04259

§ 371 Date: Jun. 5, 1996

§ 102(e) Date: Jun. 5, 1996

[87] PCT Pub. No.: WO95/18093

PCT Pub. Date: Jul. 6, 1995

[30] Foreign Application Priority Data

Dec. 27, 1993 [AT] Austria ................ 2625/93

[51] Int. Cl.$^6$ .................. C07B 7/02; C07B 7/04; C07D 209/36; C07D 209/42
[52] U.S. Cl. ................ 548/457; 548/459; 548/492
[58] Field of Search ................ 548/457, 459, 548/492

[56] References Cited

U.S. PATENT DOCUMENTS 3,073,821  1/1963  Jöhl et al. ................ 548/459
4,073,804  2/1978  Hearon et al. ................ 548/459
5,015,760  5/1991  Sajtos ................ 560/186

FOREIGN PATENT DOCUMENTS 365385  12/1962  Switzerland .

OTHER PUBLICATIONS

*Chemical Abstracts*, vol. 99, Abstract No. 99:5513y (1983).

Pfeiffer et al., *Liebigs. Ann. Chem.*, pp. 564–589 (1980).

*Primary Examiner*—Johann Richter
*Assistant Examiner*—Jane C. Osweecki
*Attorney, Agent, or Firm*—Wenderoth, Lind & Ponack

[57] ABSTRACT

Process for the preparation of an N-substituted glycine ester or an N-substituted glycine acid by reaction of a glyoxylic acid ester half-acetal (hemiacetal) or glyoxylic acid half-acetal (hemiacetal) with an amine and hydrogenation of the intermediate product formed by this reaction, and the use of the process in a process for the preparation of indoxyl and indigo derivatives by cyclization of an N-arylglycine ester, prepared by the above process, in a molten alkali metal carbonate or alkaline earth metal carbonate with or without addition of an alkali metal amide, and if appropriate oxidation of the indoxyl derivative formed by this reaction to give the corresponding indigo derivative.

10 Claims, No Drawings

PROCESS FOR THE PREPARATION OF N-SUBSTITUTED GLYCINE ACIDS OR GLYCINE ESTERS AND THE USE OF THE PROCESS FOR INDIGO SYNTHESIS

This application is a 371 of PCT/EP 94/04259 filed Dec. 21, 1994.

Indigo has been prepared worldwide for a long time from N-phenylglycine, which is oxidized via indoxyl to give indigo. According to Ullmann, volume A 14, 149 to 156; the N-phenylglycine needed for this is prepared essentially either by reaction of monochloroacetic acid with aniline or anthranilic acid or by hydrolysis of N-cyanomethylaniline. For preparation of N-cyanomethylaniline, hydrocyanic acid or sodium cyanide is reacted with dianilinomethane here. However, working with monochloroacetic acid or with cyanides is undesirable for safety and environmental protection reasons.

It has now been found, unexpectedly, that indoxyl can be prepared not only from N-phenylglycine but also from N-phenylglycine esters, and that N-substituted glycine esters and also N-substituted glycine acids can be prepared by an environment-friendly route by reaction of an amine with a glyoxylic acid ester half-acetal (hemiacetal) or a glyoxylic acid half-acetal. Glyoxylic acid eater half-acetals and glyoxylic acid half-acetals (hemiacetal) can be produced on a large industrial scale by an environment-friendly route by ozonolysis of maleic acid derivatives and hydrogenation of the peroxidic reaction solution, for example in accordance with U.S. Pat. No. 5,015,760.

The invention therefore relates to a process for the preparation of N-substituted glycine acids or glycine esters of the formula

$$R_1R_2N\text{—}CH_2\text{—}COOR \qquad I$$

in which R is hydrogen or a straight-chain or branched alkyl group having 1 to 10 C atoms and $R_1$ and $R_2$ independently of one another are hydrogen, a substituted or unsubstituted alkyl group or a substituted or unsubstituted aryl group where $R_1$ and $R_2$ are not simultaneously hydrogen, which comprises reacting a glyoxylic acid ester half-acetal or glyoxylic acid half-acetal of the formula

$$R_3O(OH)CH\text{—}COOR \qquad II$$

in which R has the abovementioned meaning and $R_3$ is an alkyl group having 1 to 4 C atoms, with an amine of the formula

$$R_1R_2NH \qquad III$$

in which $R_1$ and $R_2$ have the abovementioned meaning, in a diluent at temperatures from 0° C. up to the reflux temperature of the diluent used, and treating the reaction product with hydrogen under pressure in the presence of a hydrogenation catalyst and a diluent, the N-substituted glycine ester or the N-substituted glycine acid of the formula I being formed, and, if desired, isolating this from the reaction mixture and if appropriate converting it into a salt or, in the case of the glycine ester, into the free acid.

In the formulae I to III, R is hydrogen or a straight-chain or branched alkyl group having 1 to 10 C atoms, preferably having 1 to 4 C atoms, especially preferably having 1 or 2 C. atoms, and $R_3$ is an alkyl group having 1 to 4 C atoms, preferably having 1 or 2 C atoms, where R and $R_3$ particularly preferably have the same meaning. $R_1$ and $R_2$ independently of one another are hydrogen, an alkyl group or an aryl group, where $R_1$ and $R_2$ are not simultaneously hydrogen. Alkyl group here is to be understood as a straight-chain, branched or cyclic alkyl group having 1 to 22 C atoms, which can be unsubstituted or substituted by alkoxy groups having 1 to 4 C atoms or by phenyl groups, for example the methyl, ethyl, n-propyl, butyl, octyl, dodecyl or hexadecyl group or isomers thereof, such as iso-propyl, iso-butyl, 2-ethylhexyl or iso-dodecyl groups, or benzyl or ethylphenyl groups. Alkoxy groups are, for example, methoxy, ethoxy, butoxy or iso-butoxy groups. An aryl group is a phenyl or naphthyl group which is unsubstituted or substituted by halogen, by alkyl groups, preferably having 1 to 6 atoms, particularly preferably having 1 to 4 C atoms, or by alkoxy groups, preferably having 1 to 4 C atoms, a phenyl group being preferred. Halogen is fluorine, chlorine or bromine. Preferably, $R_1$ is hydrogen and $R_2$ is an aryl group, preferably a phenyl or naphthyl group which is unsubstituted or substituted by halogen, by alkyl groups having 1 to 4 C atoms or by alkoxy groups having 1 to 4 C atoms, particularly preferably a phenyl or naphthyl group which is unsubstituted or substituted by alkyl groups.

The preferred N-substituted glycine acids and glycine esters accordingly include compounds of the formula

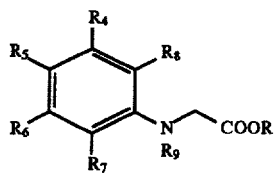

in which R has the meaning given in the formula I, $R_4$, $R_5$, $R_6$, $R_7$ and $R_8$ independently of one another are hydrogen, halogen, alkyl groups having 1 to 6 C atoms or alkoxy groups having 1 to 4 C atoms, or $R_5$ and $R_6$ or $R_6$ and $R_7$ or $R_4$ and $R_8$, together with the two particular C atoms on which they are substituted, are a benzene ring which is unsubstituted or substituted by halogen, alkyl groups having 1 to 6 C atoms or alkoxy groups having 1 to 4 C atoms, and $R_9$ is hydrogen, an alkyl radical having 1 to 6 C atoms, which can optionally be substituted, or an aryl radical, which can optionally be substituted by halogen, alkyl groups or alkoxy groups.

To prepare the compounds of the formula I, a glyoxylic acid ester half-acetal or glyoxylic acid half-acetal of the formula II is first heated and reacted with an amine of the formula III at temperatures from 0° C., preferably from room temperature, up to the reflux temperature of the diluent used, if appropriate under pressure. Diluents are preferably to be understood as meaning alcohols, such as methanol, ethanol, iso-propanol and butanol. That alcohol in which the alkyl part corresponds to the alkyl parts in the glyoxylic acid ester half-acetal preferably used is preferably employed as the diluent.

At least 1 mol, but in general 1 to 5 mol, preferably 1 to 3 mol, particularly preferably 1 to 1.5 mol, of amine of the formula III are employed here per mol of glyoxylic acid ester half-acetal or glyoxylic acid half-acetal of the formula II. The reaction is preferably carried out under normal pressure, but pressures from 1 to 20 bar can be applied.

The reaction is monitored in the customary manner, preferably by chromatography. When the reaction has ended, which is detected by the disappearance of the particular half-acetal from the reaction mixture, the reaction mixture is cooled. The intermediate compound formed, which has not been identified chemically, but is probably a compound of the formula $R_1R_2$—N—C(OH) (OR$_3$)—COOR, $R_1R_2$—N—CH(OH)—COOR, $R_1R_2$—N—CH(OR$_3$)—COOR or, in the case where, for example, $R_2$ is a hydrogen atom, a compound of the formula $R_1$N=CH—COOR, in which R, $R_1$, $R_2$ and $R_3$ in the compounds mentioned have the abovementioned meaning, can be isolated by evaporating off the diluent and if appropriate purified, for example with the aid of extraction, distillation or chromatography. However, it has proved to be advantageous that the reaction mixture can be subjected to the hydrogenation directly and without isolation of the intermediate product.

The hydrogenation of the intermediate compound is carried out with the aid of hydrogen in a diluent in the presence of a hydrogenation catalyst. Suitable diluents are diluents which are inert under the reaction conditions, for example aliphatic hydrocarbons, such as hexane or pentane, aromatic hydrocarbons, such as toluene or xylenes, ethers, such as iso-propyl ether, methyl-tert-butyl ether, tetrahydrofuran or dioxane, pyridine, water and alcohols or mixtures of such diluents, preferably aliphatic alcohols having 1 to 8 C atoms, for example methanol, ethanol, iso-propanol, butanol, hexanol or octanol. The diluent is employed in an excess relative to the intermediate compound, preferably in a 5- to 30-fold excess, based on the weight. The intermediate compound must be soluble in the diluent.

Catalysts which are capable of catalyzing the splitting off of half-acetal, hydroxyl or alkoxy groups from a C atom when hydrogen is supplied or which are capable of catalyzing the hydrogenation of enamines to give amines are used as the hydrogenation catalyst. Such catalysts contain, as the active component, metals, such as, for example, nickel, cobalt, platinum or palladium, or chemical compounds of such metals, for example oxides, which can be alloyed, intermingled or coated with one another and/or with other metals or metal compounds, for example iron, rhodium or copper. The catalyst preferably comprises nickel as the active Constituent. The catalyst can be employed here as such, in a form applied to a customary support material or to a monolithic support, or if appropriate as a fixed bed catalyst, and is preferably employed in a form applied to a support.

In general, at least 0.5 g of catalyst is used per mol of intermediate compound. Since the optimum amount of the catalyst depends on its efficiency, however, it may be of advantage to employ larger or smaller amounts of catalyst.

The optimum catalyst and the optimum amount of Catalyst can easily be determined by simple preliminary experiments with various amounts of catalysts of known specificity.

The hydrogen is introduced into the reaction mixture in the customary manner, and the hydrogen is advantageously forced onto the reaction mixture comprising the intermediate compound, diluent and hydrogenation catalyst. A hydrogen pressure from 1 to 120 bar, preferably from 20 to 100 bar, particularly preferably from 40 to 80 bar, is established here.

The hydrogenation is carried out at temperatures from about 10° C. to about 150° C., preferably between about 20° C. and 130° C.

The N-substituted glycine ester or the N-substituted glycine acid of the formula I is formed in high yields in this reaction. The reaction is monitored with the aid of suitable methods, preferably by chromatography. When the reaction has ended, the N-substituted glycine ester or the N-substituted glycine acid can be isolated from the reaction mixture by evaporation of the diluent and if appropriate purified with the aid of customary methods, such as extraction, chromatography or distillation. In general, however, the purity of the resulting N-substituted glycine ester and the N-substituted glycine acid is very high and therefore adequate for most purposes without a purification step. The reaction mixture, which comprises, for example, the N-phenylglycine ester, can therefore be employed directly in any desired further reaction.

If appropriate, the N-substituted glycine ester and the N-substituted glycine acid can be converted into a salt, for example an alkali metal or alkaline earth metal salt, in a known manner. Preferred salts are the Na and the K salt. The glycine ester can furthermore be converted, if desired, into the free acid in a known manner.

In a particularly preferred embodiment of the process, a glyoxylic acid ester half-acetal in which the two alkyl groups are identical and in each case are a straight-chain alkyl group having 1 to 4 C atoms is heated at the reflux temperature under normal pressure with an amine of the formula $R_1NH_2$ in which $R_1$ is a phenyl or naphthyl group which is unsubstituted or substituted by halogen, by alkyl groups having 1 to 4 C atoms or by alkoxy groups having 1 to 4 C atoms in a molar ratio of 1:1 to 1.5 in an alkyl alcohol in which the alkyl part corresponds to the alkyl parts in the glyoxylic acid ester half-acetal employed. The reaction is monitored by chromatography. When the glyoxylic acid ester half-acetal has disappeared from the reaction mixture, a hydrogenation catalyst which comprises nickel as the active constituent and is applied to a support is introduced into the reaction mixture and hydrogen is forced in with a pressure of 40 to 80 bar. The reaction is monitored by chromatography. When the reaction has ended, the N-phenylglycine ester formed is isolated, if appropriate, by evaporating off the diluent and if appropriate is further purified in the customary manner, for example by extraction, distillation or chromatography, or the reaction mixture which comprises the N-phenylglycine ester is employed directly in any desired further reaction.

The N-substituted glycine ester and the N-substituted glycine acid of the formula I can be used for synthesis of the most diverse chemical compounds, for example for intermediate products for herbicides, or for synthons or pharmaceutical intermediate products. N-arylglycine esters prepared by the process according to the invention are preferably employed for the preparation of corresponding indoxyl derivatives and furthermore for the preparation of corresponding indigo derivatives. In fact, it has been found, unexpectedly, that it is possible to carry out cyclization of an N-arylglycine to give indoxyl directly, that is to say without prior hydrolysis of the ester groups.

The invention therefore also relates to a process for the preparation of an indoxyl derivative of the formula

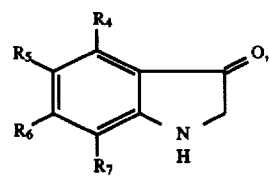

IV in which $R_4$, $R_5$, $R_6$ and $R_7$ independently of one another are hydrogen, halogen, alkyl groups having 1 to 6 C atoms or alkoxy groups having 1 to 4 C atoms, or $R_5$ and $R_6$ or $R_6$ and $R_7$, together with the two particular C atoms on which they are substituted, are a benzene ring which is unsubstituted or substituted by halogen, alkyl groups having 1 to 6 C atoms or alkoxy groups having 1 to 4 C atoms, which comprises preparing an N-arylglycine ester of the formula

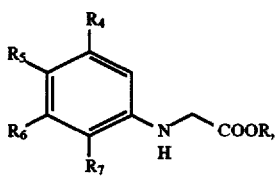

in which R has the meaning given in the formula I and $R_4$, $R_5$, $R_6$ and $R_7$ have the abovementioned meaning, as described above and cyclizing it with or without isolation, in the presence of molten alkali metal hydroxide or alkaline earth metal hydroxide, with or without addition of an alkali metal amide, at temperatures from 150° to 300° C. to give the indoxyl of the formula IV.

Preferably, in the formula IV, $R_4$, $R_5$, $R_6$ and $R_7$ are hydrogen, halogen, alkyl groups having 1 to 4 C atoms or alkoxy groups having 1 to 4 C atoms, particularly preferably hydrogen or alkyl groups.

The cyclization of the N-arylglycine ester can be carried out here unexpectedly as with arylglycines themselves, for example in the manner described according to Römpps Chemie Lexikon [Römpps Chemical Dictionary], page 1861 et seq., which discloses the cyclization with $NaNH_2$ of phenylglycine with subsequent oxidation, the alkyl ester group of the N-substituted glycine ester being split off as an alcohol.

The invention furthermore relates to a process for the preparation of an indigo derivative of the formula

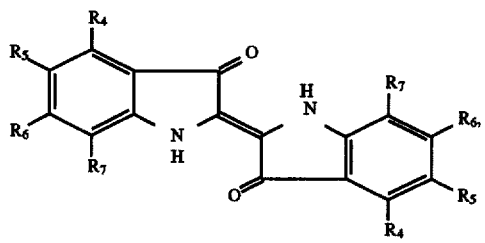

in which $R_4$, $R_5$, $R_6$ and $R_7$ have the meaning given in formula IV, which comprises preparing, according to the invention, an indoxyl derivative of the formula IV in which $R_4$, $R_5$, $R_6$ and $R_7$ have the abovementioned meaning and oxidizing this in the customary manner, preferably, for example, in accordance with Chemische Berichte, Volume 99, 1966, pages 2146–2154, to give the indigo derivative of the formula V, i.e. more specifically, this reference discloses oxidation with $O_2$ (air) of the indoxyl derivative of formula IV to the indigo derivative of formula V.

N-Substituted glycine esters and indoxyl and indigo compounds can be prepared in good yields by an environment-friendly route in the manner described. The process according to the invention therefore represents an enrichment of the art.

EXAMPLES

General Preparation Instructions 0.375 mol of the amine of the formula III was dissolved in about 9 to 13 times the amount by weight of methanol, 0.375 mol of glyoxylic acid methyl ester methyl hemi-acetal (GMHA) (45 g) or 0.375 mol of glyoxylic acid methyl hemi-acetal (GAHA) (39.75 g), dissolved in about 12 times the amount by weight of methanol, is added and the mixture is allowed to react at 25° to 45° C. The progress of the reaction was monitored by means of thin layer chromatography. When the reaction had ended, the reaction solution was fed into a hydrogenation reactor and subjected to hydrogenolysis at a temperature of about 115° C. under a hydrogen pressure of about 60 bar by means of a nickel catalyst, which was applied to a support (Ni 6458 from Engelhardt). The reaction was monitored by thin layer chromatography. When the reaction had ended, the catalyst was filtered off and the diluent was distilled off. Since the purity of the N-substituted glycine esters obtained in this reaction was very high and in some cases exceeded 99%, it was possible to omit further purification. N-substituted glycine esters or glycine acids prepared in accordance with the general preparation instructions and the yields obtained are shown in Table 1. The resulting N-substituted glycine esters and glycine acids and their purity were characterized by gas chromatography, by comparison with the chemically pure substances.

TABLE 1

| Example | A | B | P | Yield |
|---|---|---|---|---|
| 1 | 34.8 g of aniline | 45 g of GMHA | 62 g of N-phenylglycine acid methyl ester | 100 |
| 2 | 40.9 g of 4-hydroxyaniline | 45 g of GMHA | 67 g of N-4-hydroxyphenylglycine methyl ester | 99 |
| 3 | 56.6 g of anthranilic acid methyl ester | 45 g of GMHA | 56 g of N-2-carbomethoxy-phenylglycine acid methyl ester | 99 |
| 4 | 53.6 g of 1-naphthylamine | 45 g of GMHA | 62 g of N-naphthylglycine acid methyl ester | 69 |
| 5 | 40.1 g of benzylamine | 45 g of GMHA | 67 g of N-benzylglycine acid methyl ester | 100 |
| 6 | 34.8 g of aniline | 39.75 g of GAHA | 53.7 g of N-phenylglycine acid | 95 |

In Table 1 the abbreviations are as follows

A: Amount and nature of the amine of the formula III

B: Amount of glyoxylic acid ester half-acetal or glyoxylic acid half-acetal

P: Amount and nature of the N-substituted glycine ester obtained as the product

Yield: Yield in % of theory, based on the amine of the formula III employed

Example 7

0.5 g of N-phenylglycine acid methyl ester, prepared in the manner described in Example 1, was introduced into a hot melt of 2.5 g of potassium hydroxide, into which 0.3 g of sodium amide had been introduced and which had a temperature of about 260° to 270° C., and allowed to react for a few minutes. The indoxyl/potassium hydroxide melt formed by this procedure was introduced into ice-water. 0.3 g of indigo was obtained by introducing air into the aqueous suspension and filtering off and drying the precipitate formed.

What I claimed is:

1. A process for the preparation of an N-substituted glycine ester or an N-substituted glycine acid of the formula

$$R_1R_2N\text{—}CH_2\text{—}COOR \quad \text{I}$$

in which R is hydrogen or a straight-chain or branched alkyl group having 1 to 10 C atoms and $R_1$ and $R_2$ independently of one another are hydrogen, a substituted or unsubstituted alkyl group or a substituted or unsubstituted aryl group where $R_1$ and $R_2$ are not simultaneously hydrogen, which comprises reacting a glyoxylic acid ester half-acetal or glyoxylic acid half-acetal (hemiacetal) of the formula

$$R_3(OH)CH\text{—}COOR \quad \text{II}$$

in which R has the abovementioned meaning and $R_3$ is an alkyl group having 1 to 4 C atoms, with an amine of the formula

$$R_1R_2NH \quad \text{III}$$

in which $R_1$ and $R_2$ have the abovementioned meaning, in a diluent at temperatures from 0° C. up to the reflux temperature of the diluent used, and treating the resulting intermediate product with hydrogen under pressure in the presence of a hydrogenation catalyst and a diluent, the N-substituted glycine ester or the N-substituted glycine acid of the formula I being formed, and, if desired, isolating this from the reaction mixture and if appropriate converting it into a salt or, in the case of the glycine ester, into the free acid.

2. The process as claimed in claim 1, wherein a compound of the formula II in which R and $R_3$ are identical and are alkyl groups having 1 to 4 C atoms is employed.

3. The process as claimed in claim 1, wherein a compound of the formula III in which $R_1$ is a phenyl or naphthyl group which is unsubstituted or substituted by halogen, by alkyl groups having 1 to 6 C atoms or by alkoxy groups having 1 to 4 C atoms and $R_2$ is hydrogen is employed.

4. The process as claimed in claim 1, wherein a pressure of 40 to 80 bar and a temperature of 20° to 130° C. is maintained during the hydrogenolysis.

5. The process as claimed in claim 1, wherein a compound of the formula III in which $R_1$ is a phenyl or naphthyl group which is unsubstituted or substituted by alkyl groups having 1 to 4 C atoms and $R_2$ is hydrogen is employed.

6. The process as claimed in claim 1, wherein 1 to 1.5 mol of the compound of the formula III are employed per mol of the compound II.

7. The process as claimed in claim 1, wherein an aliphatic alcohol having 1 to 4 C atoms, the alkyl part of which corresponds to the alkyl parts in the glyoxylic acid ester half-acetal hemiacetal employed is employed as the diluent.

8. A process for the preparation of an indoxyl derivative of the formula

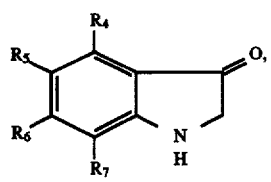

IV in which $R_4$, $R_5$, $R_6$ and $R_7$ independently of one another are hydrogen, halogen, alkyl groups having 1 to 6 C atoms or alkoxy groups having 1 to 4 C atoms, or $R_5$ and $R_6$ or $R_6$ and $R_7$, together with the two particular C atoms on which they are substituted, are a benzene ring which is unsubstituted or substituted by halogen, alkyl groups having 1 to 6 C atoms or alkoxy groups having 1 to 4 C atoms, which comprises preparing an N-arylglycine ester of the formula

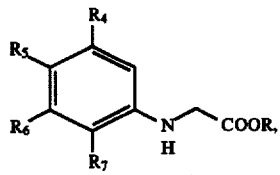

Ib in which R has the meaning given in the formula I as claimed in claim 1 and $R_4$, $R_5$, $R_6$ and $R_7$ have the above-mentioned meaning, as claimed in claim 1 and cyclizing it, in the presence of molten alkali metal hydroxide or alkaline earth metal hydroxide, with or without addition of an alkali metal amide, at temperatures from 150° to 300° C. to give the indoxyl of the formula IV.

9. The process as claimed in claim 8, wherein an N-arylglycine ester of the formula Ib in which R is an alkyl group having 1 to 4 C atoms and $R_4$, $R_5$, $R_6$ and $R_7$ independently of one another are hydrogen, halogen, alkyl groups having 1 to 4 C atoms or alkoxy groups having 1 to 4 C atoms is employed.

10. A process for the preparation of an indigo derivative of the formula

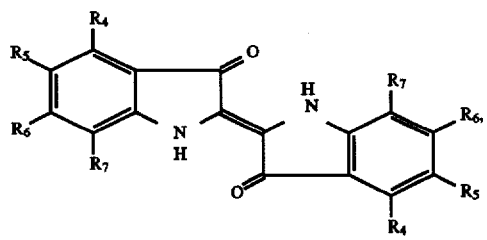

V in which $R_4$, $R_5$, $R_6$ and $R_7$ have the meaning given in formula IV as claimed in claim 8, which comprises preparing, as claimed in claim 8, an indoxyl derivative of the formula IV as claimed in claim 8 and oxidizing this to give the indigo derivative of the formula V.

* * * * *